US012653321B2

(12) United States Patent
Manwaring et al.

(10) Patent No.: US 12,653,321 B2
(45) Date of Patent: Jun. 16, 2026

(54) DEVICE AND METHOD TO INDUCE VIBRATIONAL WAVEFORMS THAT HETERODYNE IN THE BODY TO IMPROVE SLEEP ONSET AND SLEEP QUALITY

(71) Applicant: Brigham Young University, Provo, UT (US)

(72) Inventors: Kim H. Manwaring, Heber City, UT (US); Jonathan D. Blotter, Heber City, UT (US); Scott Steffensen, Provo, UT (US); Jeffrey B. Feland, Spanish Fork, UT (US); Kyle B. Bills, Springville, UT (US)

( * ) Notice: Subject to any disclaimer, the term of this patent is extended or adjusted under 35 U.S.C. 154(b) by 1301 days.

(21) Appl. No.: 17/359,373

(22) Filed: Jun. 25, 2021

(65) Prior Publication Data

US 2021/0401184 A1     Dec. 30, 2021

Related U.S. Application Data

(60) Provisional application No. 63/186,035, filed on May 7, 2021, provisional application No. 63/044,019, filed on Jun. 25, 2020.

(51) Int. Cl.
| | |
|---|---|
| *A47C 21/00* | (2006.01) |
| *A61M 21/00* | (2006.01) |
| *A61M 21/02* | (2006.01) |

(52) U.S. Cl.
CPC .......... *A47C 21/006* (2013.01); *A61M 21/02* (2013.01); *A61M 2021/0022* (2013.01); *A61M 2210/0637* (2013.01); *A61M 2230/63* (2013.01)

(58) Field of Classification Search
CPC ................ A47C 21/006; A61M 21/02; A61M 2021/0022; A61M 2210/0637; A61M 2230/63; A61M 16/049
(Continued)

(56) References Cited

U.S. PATENT DOCUMENTS

| | | | |
|---|---|---|---|
| 3,934,283 | A | 1/1976 | Raffel |
| 5,140,977 | A | 8/1992 | Raffel |

(Continued)

OTHER PUBLICATIONS

Koob, George F.; "Dopamine, addiction and reward"; Seminars in The Neurosciences; 1992; vol. 4; pp. 139-148.
(Continued)

*Primary Examiner* — Sunita Reddy
(74) *Attorney, Agent, or Firm* — Barnes & Thornburg LLP; Ryan L. Marshall

(57) ABSTRACT
A system for introducing vibrational waves into a body of a subject to treat sleep disorders is provided. The system includes a bed frame having a first vibration contact and a second vibration contact. The first vibration contact is in mechanical communication with a first location of the body of the subject, and the second vibration contact is in mechanical communication with a second location of the body of the subject. A first vibration source is connected to the first vibration contact and configured to cause a first vibration of the first vibration contact. A second vibration source is connected to the second vibration contact and configured to cause a second vibration of the second vibration contact. The location or orientation of the first vibration contact and the second vibration contact are configured such that the first vibration combines with the second vibration to generate a super-imposed vibration.

15 Claims, 6 Drawing Sheets

(58) Field of Classification Search

USPC ..................................................... 600/26–28

See application file for complete search history.

(56) References Cited

U.S. PATENT DOCUMENTS

| | | | | |
|---|---|---|---|---|
| 5,973,422 | A * | 10/1999 | Clamme | H02K 33/16 |
| | | | | 310/90.5 |
| 8,144,001 | B1 * | 3/2012 | D'Souza | A47C 31/105 |
| | | | | 340/573.1 |
| 2003/0040679 | A1 | 2/2003 | Weber et al. | |
| 2006/0047230 | A1 * | 3/2006 | Talish | A61H 1/001 |
| | | | | 601/49 |
| 2009/0128306 | A1 * | 5/2009 | Luden | H04N 21/43074 |
| | | | | 340/407.1 |
| 2011/0010860 | A1 * | 1/2011 | Grimes | A61H 1/005 |
| | | | | 5/616 |
| 2012/0203149 | A1 | 8/2012 | Grimes et al. | |
| 2013/0106205 | A1 * | 5/2013 | Clamme | H02K 33/02 |
| | | | | 310/15 |
| 2015/0305975 | A1 * | 10/2015 | Maffei | A47C 7/024 |
| | | | | 601/56 |
| 2016/0242995 | A1 * | 8/2016 | Karkkainen | A61H 23/02 |
| 2017/0112716 | A1 | 4/2017 | Rawls-Meehan | |
| 2017/0173481 | A1 * | 6/2017 | Nielsen | A61H 23/0236 |
| 2019/0099009 | A1 | 4/2019 | Connor | |
| 2019/0290011 | A1 | 9/2019 | Fratila | |
| 2020/0222262 | A1 * | 7/2020 | Northen | A61H 23/0263 |

OTHER PUBLICATIONS

Schultz, Wolfram, et al.; "A Neural Substrate of Prediction and Reward"; Science ; Mar. 14, 1997; New Series; vol. 275, No. 5306; pp. 1593-1599.

Phillips, Anthony G., et al.; "Amygdalar control of the mesocorticolimbic dopamine system: parallel pathways to motivated behavior"; Neuroscience and Biobehavioral Reviews; 2003; 27; pp. 543-554.

Agmo, Anders, et al. ; "Reward and Reinforcement Produced by Drinking Sucrose: Two Processes That May Depend on Different Neurotransmitters"; Pharmacology Biochemistry and Behavior; 1995; vol. 52, No. 2; pp. 403-414.

Oleson, Erik B. ,et al .; "Subsecond Dopamine Release in the Nucleus Accumbens Predicts Conditioned Punishment and Its Successful Avoidance"; The Journal of Neuroscience; Oct. 17, 2012; 32(42); pp. 14804-14808.

Howe, Mark W.; "Prolonged dopamine signalling in striatum signals proximity and value of distant rewards"; Nature; Research Letter; Aug. 29, 2013; vol. 500; pp. 575-590; doi:10.1038/nature12475.

Schultz, Wolfram, et al.; "Responses of Monkey Dopamine Neurons to Reward and Conditioned Stimuli during Successive Steps of Learning a Delayed Response Task"; The Journal of Neuroscience; Mar. 1993; 13(3); pp. 900-913.

Di Chiara, Gaetano, et al.; "Drugs abused by humans preferentially increase synaptic dopamine concentrations in the mesolimbic system of freely moving rats"; Neurobiology; Proc. Natl. Acad. Sci.; Jul. 1988; vol. 85; pp. 5274-5278.

Le Moal, Michel, et al.; "Drug addiction: Pathways to the disease and pathophysiological perspectives"; European Neuropsychopharmacology; 2007; 17; pp. 377-393.

Koob, George F., et al.; "Neurocircuitry of Addiction"; Neuropsychopharmacology Reviews; 2010; 35; pp. 217-238.

Koob, George F., et al.; "Neurobiology of addiction: a neurocircuitry analysis"; Lancet Psychiatry; Aug. 2016; 3(8); pp. 760-773; doi:10.1016/S2215-0366(16)00104-8.

Imperato, Assunta, et al.; "Dopamine Release and Metabolism in Awake Rats After Systemic Neuroleptics as Studied By Trans-Striatal Dialysis"; The Journal of Neuroscience; Feb. 1985; vol. 5, No. 2; pp. 297-306.

Yim, Hyeon Joo, et al.; "Ethanol-induced increases in dopamine extracellular concentration in rat nucleus accumbens are accounted for by increased release and not uptake inhibition"; Alcohol; 2000; 22; pp. 107-115.

Weiss, Friedbert, et al.; "Ethanol Self-Administration Restores Withdrawal-Associated Deficiencies in Accumbal Dopamine and 5-Hydroxytryptamine Release in Dependent Rats"; The Journal of Neuroscience; May 15, 1996; 16(10); pp. 3474-3485.

Nestler, Eric J.; "Psychogenomics: Opportunities for Understanding Addiction"; The Journal of Neuroscience; Nov. 1, 2001; 21(21); pp. 8324-8327.

Kalivas, Peter W., et al.; "The Neural Basis of Addiction: A Pathology of Motivation and Choice"; Am J Psychiatry; Aug. 2005; 162:8; pp. 1403-1413.

Diana, Marco, et al.; "Crucial Role of Acetaldehyde in Alcohol Activation of the Mesolimbic Dopamine System"; Ann. N. Y. Acad. Sci. 1139: 307-317 (2008). 2008 New York Academy of Sciences; doi: 10.1196/annals.1432.009.

Steffensen, Scott C., et al.; "Cocaine disinhibits dopamine neurons in the ventral tegmental area via use-dependent blockade of GABA neuron voltage-sensitive sodium channels"; European Journal of Neuroscience; 2008; vol. 28; pp. 2028-2040; doi:10.1111/j.1460-9568.2008.06479.x.

Olsson, Sara K., et al.; "Elevated levels of kynurenic acid change the dopaminergic response to amphetamine: implications for schizophrenia"; International Journal of Neuropsychopharmacology; 2009; 12; pp. 501-512; doi:10.1017/S1461145708009383.

Hyman, Steven E., et al.; "Addiction and the Brain: the Neurobiology of Compulsion and Its Persistence"; Neuroscience; Nature Reviews; Oct. 2001; vol. 2; pp. 695-703.

Hyman, Steve E., et al.; "Neural Mechanisms of Addiction: The Role of Reward-Related Learning and Memory"; Neural Mechanisms of Addiction; Annu. Rev. Neurosci. 2006. 29:565-598. Downloaded from www.annualreviews.org.

Nugent, Fereshteh S., et al.; "LTP of GABAergic synapses in the ventral tegmental area and beyond"; J Physiol; 2008; 586.6; pp. 1487-1493.

Piper, Megan E., et al.; "Anxiety Diagnoses in Smokers Seeking Cessation Treatment: Relations with Tobacco Dependence, Withdrawal, Outcome, and Response to Treatment"; Addiction; Feb. 2011; 106(2); pp. 418-427; doi:10.1111/j.1360-0443.2010.03173.x.

Bills, Kyle B., et al.; "Targeted Subcutaneous Vibration With Single-Neuron Electrophysiology as a Novel Method for Understanding the Central Effects of Peripheral Vibrational Therapy in a Rodent Model"; Dose-Response: An International Journal; Jan.-Mar. 2019; pp. 1-7.

Martorell, Anthony J., et al.; "Multi-sensory Gamma Stimulation Ameliorates Alzheimer's-Associated Pathology and Improves Cognition"; Cell; Apr. 4, 2019; 177; pp. 256-271; https://doi.org/10.1016/j.cell.2019.02.014.

Clements-Cortes A, Ahonen H, Evans M, Freedman M, Bartel L (2016). Journal of Alzheimer's Disease, 52(2), 651-660. DOI 10.3233/JAD-160081. ref Ko et al.

Costa, Madalena, et al. 'Multiscale Entropy Analysis of Biological Signals'. Phys. Rev. E, vol. 71, American Physical Society, Feb. 2005, p. 021906, https://doi.org/10.1103/PhysRevE.71.021906.

* cited by examiner

Time (seconds)

DEVICE AND METHOD TO INDUCE VIBRATIONAL WAVEFORMS THAT HETERODYNE IN THE BODY TO IMPROVE SLEEP ONSET AND SLEEP QUALITY

CROSS REFERENCE TO RELATED APPLICATIONS

This application claims the benefit of U.S. Provisional Application No. 63/044,019, filed Jun. 25, 2020, and U.S. Provisional Application No. 63/186,035, filed May 7, 2021, the contents of which are hereby incorporated by reference.

BACKGROUND

Sleep is a natural state for the body that can be described by reduced motility and sensory responses. There are various stages of sleep, and these have been classified as non-rapid eye movement (NREM) and rapid eye movement sleep (REM). In NREM sleep there is an N1, N2, and N3 stage of sleep. These sleep stages have been identified using an electroencephalogram (EEG). EEG tests use small metal electrodes attached to the scalp to detect electrical activity in the brain. Stage N1 occurs just as a person goes into sleep and is usually less than 8 minutes. During this time, a person can be awakened easily especially due to an unexpected noise. This stage of sleep is characterized by rhythmic alpha waves in the 8-13 Hz frequency range. In Stage N2 sleep, muscles become more relaxed and slow-wave (delta) brain activity occurs. Stage N2 typically lasts for 10-25 minutes but can last for an hour. Stage N3 is called deep sleep when delta brain activity increases and in which it is harder to wake a person that can last for 20 to 40 minutes. Some sleep models actually break Stage N3 into a Stage N3 and N4. Typically, after a person has passed through these three stages of NREM sleep, they enter REM sleep which is a deeper sleep during which breathing becomes slowed and regular and the eyes and eyelids may flutter. It is common to cycle through the stages of NREM and REM sleep multiple times throughout the night. Restorative functions occur in the body during all stages of sleep. N3 and REM sleep are, however, when our bodies and minds receive the most renewal.

A heuristic model of sleep-wake states in which arousal, sleep drive, and conscious awareness were identified as the three indicators to determine a person's sleep and wake state. Arousal refers to the wake drive and is related to the relative amount of beta and alpha wave activity. Sleep drive is determined by the amount of delta wave activity. Conscious awareness can be quantified by the complexity of neural activity. REM sleep is achieved by low arousal, high sleep drive, and low conscious awareness.

Sleep disorders such as insomnia, sleep apnea, and restless leg syndrome effect an estimated 10% of the entire population. About 20-30% of adults have reported symptoms of insomnia. Insufficient or compromised sleep is a major risk factor for increased disease, depression, anxiety disorders, substance abuse, pregnancy complications, neurobehavioral and cognitive impairment.

While there are a variety of medications that have been clinically evaluated and widely used to treat insomnia, the only non-pharmacological treatment that has been clinically tested and used as primary treatment for insomnia is cognitive behavioral therapy (CBT). One benefit to non-pharmacological treatments over their counterpart is that they can produce long-lasting results with a lower chance of producing side effects. For this reason, it is important to develop viable non-pharmacological treatments for these sleep disorders.

BRIEF SUMMARY

A system for introducing vibrational waves into a body of a subject is provided herein. The system includes a bed frame comprising a first vibration contact and a second vibration contact. The first vibration contact is in mechanical communication with a first location of the body of the subject, and the second vibration contact is in mechanical communication with a second location of the body of the subject. A first vibration source is connected to the first vibration contact and configured to cause a first vibration of the first vibration contact. A second vibration source is connected to the second vibration contact and configured to cause a second vibration of the second vibration contact. The location or orientation of the first vibration contact and the second vibration contact are configured such that the first vibration combines with the second vibration to generate a super-imposed vibration.

A method of treating a sleep disorder, depression, anxiety, or multiple forms of pain in a patient is also provided. The method includes providing a bed frame comprising a first panel and a second panel in contact with a box spring or mattress, and at least two vibration wave sources. The method also includes vibrating the first panel of a bed frame in a first waveform of 5 to 200 Hz and vibrating the second panel of the bed frame in a second waveform of 5 to 200 Hz. The first and second waveforms combine to generate a super-imposed vibration in a range of 0.25 Hz to 10 Hz while the patient is positioned on the bed. The bed frame can include two or more vibration wave sources that combine to produce unique low frequency vibrational waves in the mattress and body.

DETAILED DESCRIPTION

Researchers have recently begun investigating the effects that mechanical stimulations such as whole-body vibration (WBV) and rocking have on sleep. The concept of using mechanical stimulation to induce or improve sleep largely stems from the fact that vibrating environments such as trains or cars and rocking environments such as swings can lead to higher levels of drowsiness. Despite multiple studies to ascertain the effects of vibration and rocking on sleep quality, only single frequency systems have been considered and optimal amplitudes and frequencies have not been reported. Previous attempts to provide vibrating or rocking environments resulted in relatively complicated, heavy, and expensive frames with large motors to either lift or rock the bed.

Figure 1:
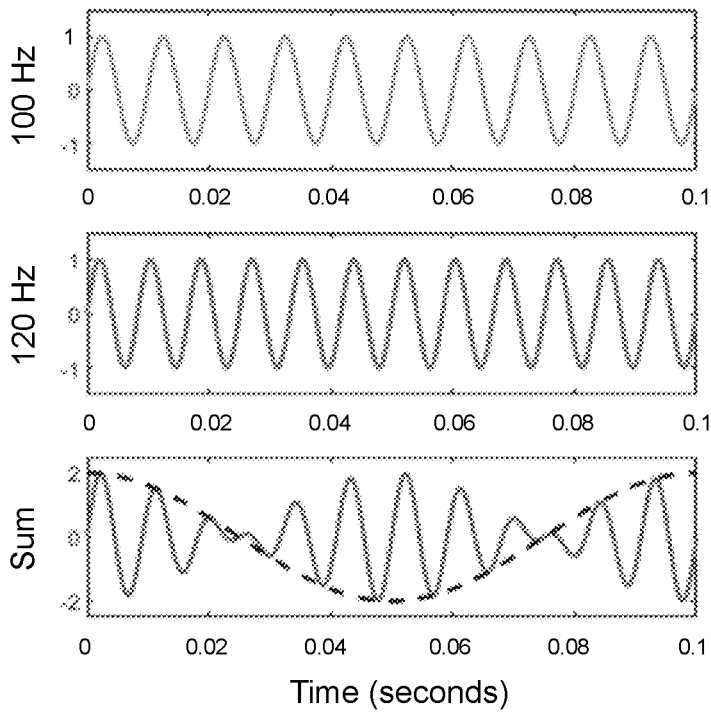
FIG. 1 shows two superimposed sinusoidal waves (100 Hz and 120 Hz) that form the harmonic response labeled Sum. The beat frequency is equal to the difference in the two inputs, which would be 20 Hz in this case.

Electric motors and electro dynamic vibration transducers cannot effectively operate at frequencies below 7 Hz. The innovation in the proposed system is that multiple vibration transducers are used to develop vibration waves and patterns that heterodyne in the mattress and human body to produce low frequency (0.05 Hz to 10 Hz) waves that travel through the body in either predictable or chaotic, unpredictable manner as desired, helping to induce sleep by lowering arousal and conscious awareness. Heterodyning of two vibration waves at different frequencies creates a new wave that oscillates at the average frequency of the two waves but that is amplitude modulated at a frequency equal to the difference between the two waves. This difference frequency is often referred to as the beat frequency. An example of a 100 Hz sine wave and a 120 Hz sine wave being superimposed to create an amplitude-modulated wave at the beat frequency of 20 Hz is shown in FIG. 1.

Electromagnetic vibration drives generally have difficulty generating low frequency (f<7 Hz) vibration. Therefore, they have shown to not be as effective for inducing sleep. To address this issue, using wave superposition or the heterodyning of multiple conventional vibration waves creates a low frequency vibrational wave. When vibration waves are superimposed in the bed system, with proper timing and phasing of the signals they can be used to produce a displacement wave that propagates along the length of the bed. In structural vibration analysis, this globally propagating vibration wave has been referred to as a traveling wave. This wave can also be designed to travel or propagate in a circular pattern, a side-to-side pattern, a diagonal pattern, and other patterns as desired. This form of traveling wave vibration has never been used in a bed system or as a sleep-inducing technique.

Although direct superposition of vibration waves to induce a beat frequency has shown to be an effective method there are other methods to create a low frequency traveling waves that are used in this sleep system. These consist of using filters such as phasers and flangers to manipulate, combine, and generate signals that result in low frequency traveling waves being induced in the mattress and human body.

A system for introducing vibrational waves into a body of a subject is provided herein. The system includes a bed frame comprising a first vibration contact and a second vibration contact. The first vibration contact is in mechanical communication with a first location of the body of the subject, and the second vibration contact is in mechanical communication with a second location of the body of the subject. A first vibration source is connected to the first vibration contact and configured to cause a first vibration of the first vibration contact. A second vibration source is connected to the second vibration contact and configured to cause a second vibration of the second vibration contact. The location or orientation of the first vibration contact and the second vibration contact are configured such that the first vibration combines with the second vibration to generate a super-imposed vibration.

In some embodiments, the first vibration contact is a first panel positioned beneath a box spring or a mattress and the second vibration contact is a second panel positioned beneath the box spring or the mattress.

In some embodiments, the first and second vibration source are affixed to an undersurface of the first panel and the second panel to independently vibrate each of the first and second panels in a frequency range of 5 to 200 Hz, and transmit vibrational waves to a subject that are combined by superposition in the subject.

In some embodiments, each panel can be vibrated independently in a range of 5 to 200 Hz with waveforms, which can be arbitrary, sinusoidal, triangular, rectangular with various duty cycles, or with a customized waveform shape and with sufficient power to induce subjective perception of vibration.

In some embodiments, the waveform is arbitrary. In some embodiments, the waveform is sinusoidal. In some embodiments, the waveform is triangular. In some embodiments, the waveform is rectangular with various duty cycles.

In some embodiments, each panel can be vibrated at a same frequency with 0° to 180° of relative phase.

In some embodiments, each panel can be vibrated at frequencies offset from each other such as to induce an interferential beat frequency as a difference between two or more driving frequencies.

In some embodiments, each panel can be vibrated independently with various waveforms in a range of 5 to 200 Hz to induce beat frequencies in the range of 0.05 Hz to 200 Hz which can be perceived as traveling waves.

In some embodiments, each panel can be vibrated independently to induce localized vibrational maxima into a head, cervical spine, or other desired location in the subject by use of phased inputs or superimposed vibrational waves.

In some embodiments, each panel can be vibrated independently with sinusoidal waveform sources to induce vibration into the body optimally in a range of 0.01 Hz to 10 Hz.

In some embodiments, each panel can be vibrated independently with a vibrational wave to induce a harmonic of the vibrational wave into the body in a range of 0.25 Hz to 4 Hz. In some embodiments, each panel can be vibrated independently with a vibrational wave to induce a harmonic of the vibrational wave into the body in a range of 0.01 Hz to 200 Hz.

In some embodiments, each panel can have affixed to it or its attached LFE transducer a sensor from which an oscillatory signal can be derived to monitor drive frequency and pattern of waveform and to allow depiction of signal phase and interferential beat frequencies.

In some embodiments, the vibration sources comprise at least one of electromagnetic drivers, transducers, displacement shakers, linear resonance actuators, piezoelectric actuators, solenoids, pneumatic or hydraulic actuators, and electric motors with unbalanced weights, cams, or crankshafts.

In some embodiments, a sensor is in mechanical contact with the subject to measure the super-imposed vibration.

In some embodiments, the sensor is configured to provide a feedback signal to at least one of the first vibration source and the second vibration source in response to the super-imposed vibration.

In some embodiments, the sensor comprises mouth guard sensor to derive a measure of pattern and amplitude of induced frequencies into the body which may be customized to the subject's maxillary tooth print pattern.

In some embodiments, a derived waveform pattern from the mouth guard sensor demonstrates induced beat frequencies.

In some embodiments, the system further includes a third vibration contact connected to a third vibration source and a fourth vibration contact connected to a fourth vibration source, wherein the location or orientation of the third vibration contact and the fourth vibration contact are configured such that vibrations combine to produce a super-imposed vibration.

In some embodiments, the system includes a controller that is configured to execute a sequence of waveform parameters to produce a sequence of different perceived waveforms inside the subject over a period of time. The controller and a sensor can be in electrical communication.

A method of treating a sleep disorder in a patient is also provided. The method includes providing a bed frame comprising a first panel and a second panel in contact with a box spring or mattress, and at least two vibration wave sources. The method also includes vibrating the first panel of a bed frame in a first waveform of 5 to 200 Hz and vibrating the second panel of the bed frame in a second waveform of 5 to 200 Hz. The first and second waveforms combine to generate a super-imposed vibration in a range of 0.25 Hz to 10 Hz while the patient is positioned on the bed.

A method of treating depression in a patient is also provided. The method includes providing a bed frame comprising a first panel and a second panel in contact with a box spring or mattress, and at least two vibration wave sources. The method also includes vibrating the first panel of a bed frame in a first waveform of 5 to 200 Hz and vibrating the second panel of the bed frame in a second waveform of 5 to 200 Hz.

A method of treating anxiety in a patient is also provided. The method includes providing a bed frame comprising a first panel and a second panel in contact with a box spring or mattress, and at least two vibration wave sources. The method also includes vibrating the first panel of a bed frame in a first waveform of 5 to 200 Hz and vibrating the second panel of the bed frame in a second waveform of 5 to 200 Hz.

A method of treating multiple forms of pain in a patient is also provided. The method includes providing a bed frame comprising a first panel and a second panel in contact with a box spring or mattress, and at least two vibration wave sources. The method also includes vibrating the first panel of a bed frame in a first waveform of 5 to 200 Hz and vibrating the second panel of the bed frame in a second waveform of 5 to 200 Hz.

In some embodiments, the super-imposed vibration is in a range of 0.25 Hz to 4 Hz.

In some embodiments, the bed frame and system includes at least two vibration sources. In some embodiments, the bed frame and system includes at least three vibration sources. In some embodiments, the bed frame and system includes at least four vibration sources.

In some embodiments, the sleep disorder is insomnia, sleep apnea, or restless leg syndrome. In some embodiments, the sleep disorder is insomnia. In some embodiments, the sleep disorder is sleep apnea. In some embodiments, the sleep disorder is restless leg syndrome.

In some embodiments, the method includes inducing a low frequency traveling wave vibration to the patient.

In some embodiments, the method includes filtering vibration waves to target one or more locations of the bed frame. Examples of filters include, but are not limited to, using phasers and flangers to manipulate, combine, and generate signals that result in low frequency traveling waves being induced in the mattress and human body.

In some embodiments, the method includes controlling vibration waves to target one or more locations of the bed frame.

Figure 2:
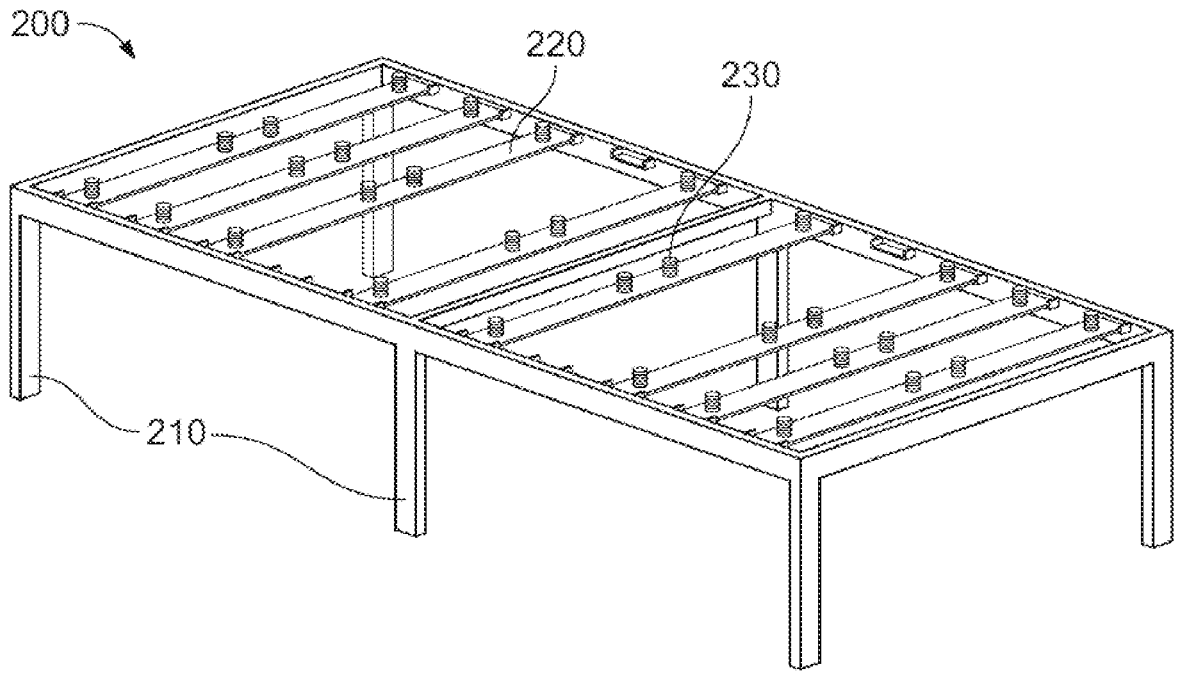
FIG. 2 shows an embodiment of a suspension system for a vibrating bed. The spheres represent individual springs or suspension and are mounted to the cross slates.

FIG. 2 shows an embodiment of a bed frame 200 without the mattress, panels, or vibration source. The legs 210 of the bed support the bed frame 200 that includes cross-slats 220. A suspension system 230 which consists of multiple springs or kinetic isolators is positioned on the cross-slats 220. Eight cross slats 220 provide support for the panels (not pictured). The small cylinders represent springs 230 that support the panels (not pictured) and provide vibration damping and isolation from one panel to the others.

Figure 3:
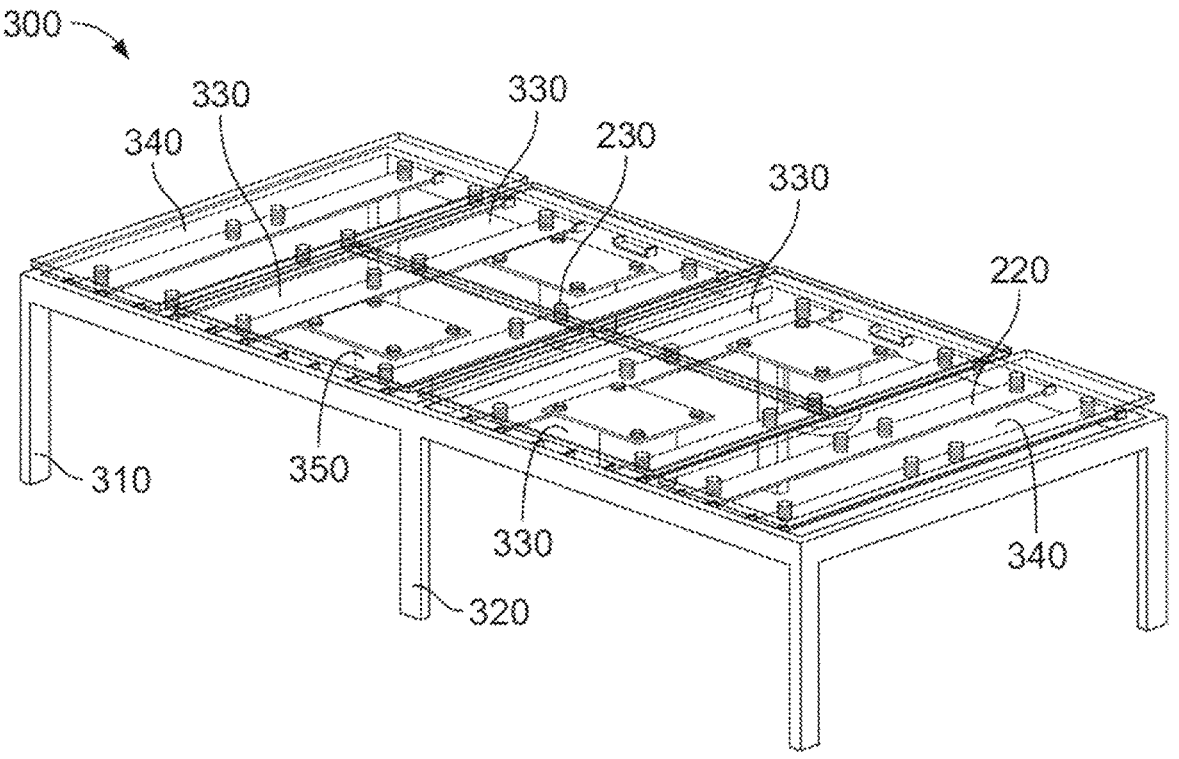
FIG. 3 shows the suspension for the vibrating bed platform with the vibrating and non-vibrating plates. This figure shows the configuration for 4 independent vibration transducers.

FIG. 3 shows an embodiment for a twin XL sized bed 300. Corner legs 310 for the bed frame 300 and a middle leg 320 are shown. The four panels 330 represent the vibration isolated and suspended vibrating panels. The panels 330 are vibration isolated from each other through a suspension system 230 thus minimizing any cross talk of vibration from one panel to the other. This allows the heterodyning of the vibration to occur in the mattress and the human body. These four panels 330 are used to generate the traveling wave vibration patterns that develop in the mattress and human body. Four springs 230 are shown on each slat 220 and for each panel 330 but this number can vary based on the size of the bed and the needed length of the slats and size of the panels. Four vibration transducers 350 are shown with one transducer mounted to each panel 330. The panels 340 at the head and foot of the bed are isolated but non-vibrating panels.

Figure 4:
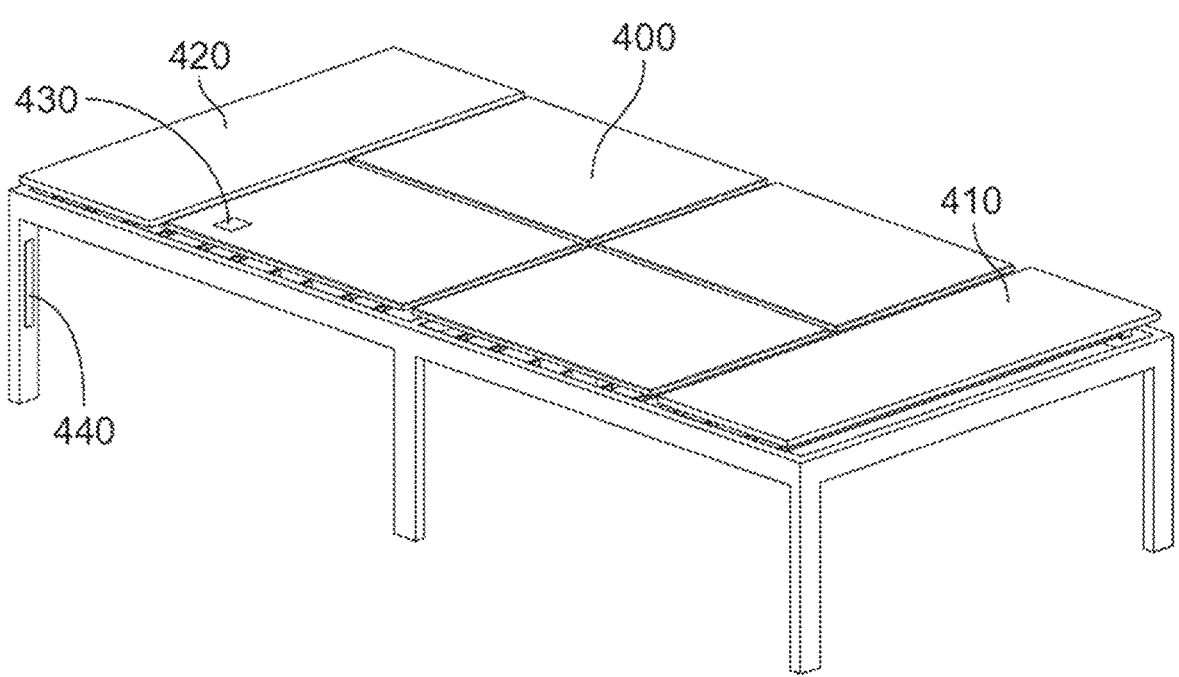
FIG. 4 shows a bed system with four individual vibration isolated sections and 2 non vibrating sections at the head and feet.

FIG. 4 shows four vibration panels 400 are shown but this number can vary based on the size of the bed (e.g. single, twin, double, queen, king) and the desired vibration pattern (e.g. rocking, circular, longitudinal). The panels 410 and 420 at the head and foot of the bed are isolated but non-vibrating panels. In some cases, the non-vibrating panel 410 at the foot of the bed is removed, and the bed system only consists of four vibrating panels 400 and non-vibrating panel at the head 420. In some embodiments, a sensor 430 may be positioned on a panel 400. The bed may include a controller 440 that is in communication with the sensor 430.

In some embodiments, the vibration sources may be from a low frequency effects (LFE) transducer, although it is understood that other vibration sources may be used including at least one of electromagnetic drivers, piezo-electric drivers, displacement shakers, solenoids, pneumatic or hydraulic actuators, and electric motors with unbalanced weights, cams, linear resonance actuators, piezoelectric actuators, or crankshafts. In some implementations, each vibration contact (e.g. each panel) can be vibrated at the same frequency with 0° to 180° of relative phase. Each vibration contact can be vibrated at frequencies offset from each other such as to induce an interferential beat frequency as the difference between the two driving frequencies. In some implementations, each vibration contact (e.g. each panel) can be vibrated with different frequencies. Each vibration contact can be vibrated independently with various waveforms in a range of 5 to 200 Hz to induce beat frequencies in the range of 0.05 Hz to 200 Hz that can be perceived as a traveling wave. As such, each vibration contact can be vibrated independently to induce localized vibrational maxima in the bed mattress. The vibration drives may also be such that the input vibration waves superimpose external to the body resulting in a beat frequency wave being directly input to the body.

The LFE transducers can induce vibration into the panel by the impulse movement of a vertically oriented magnetic piston that is controlled by a high current coil circumferentially wound. One exemplary vibration source may be the Buttkicker LFE Concert transducer which has an operating frequency range of 5 to 200 Hz (The Guitammer Company, Westerville, OH 43086).

The waveform for each transducer can be changed from sinusoidal to square or triangle or even uniquely shaped. The output voltage is amplified and applied to the LFE transducers such that a maximal induced vibration is about 3 g, but adjustable. Drive frequencies can range between 5 Hz and 250 Hz, but in some implementations more optimally in the range of 15-40 Hz. While sinusoidal waves in the therapeutic range of 45-80 Hz can be induced, in some implementations the more effective method is the employment of square waves in the 15-25 Hz range, resulting in a $3^{rd}$ harmonic at the 45-80 Hz range induced into the body by each transducer. By offsetting the frequency of the two LFE transducers, e.g. 26.7 and 27.7 Hz, a traveling interferential beat frequency pattern is induced at 1 Hz moving up and down the spine. This beat frequency can be adjusted by a difference between the two drive frequencies, typically ranging between 0.1 Hz and 10 Hz, in some implementations optimally between 0.5 to 2 Hz.

The system shown in the figures is configured to drive asymmetric, independent vibration into each panel. Two programmable function generators may control each LFE transducer independently. The programmable generators can create a first drive signal and a second drive signal. The first and second drive signals may be sinusoidal, triangular, a rectangular with variable duty cycle at frequencies, or a customized waveform between 5 and 200 Hz to correlate with the range limits of the LFE transducers. The output voltage of the function generators can be adjusted between 0 and 1.5 V, the latter for maximal drive effect. The first and second drive signals may be conditioned (e.g. amplified, strengthened, conditioned, increased in power) by an amplifier. Further, the waveform combinations between two simultaneously operating function generators can be sequenced in time to achieve various parameters in the desired frequency range of 45 to 80 Hz. Exemplary function generator may include the Resonant Light Progen II programmable function generators for this purpose (Resonant Light Technology Inc., Courtenay, BC).

The output signal of each programmable function generator passes to stereo inputs of an audio amplifier which accommodates stereo input and outputs. Each signal is amplified in the functional range of 5 Hz to 200 Hz with a maximum of 1500 W out of each channel to each of the two LFE transducers. Exemplary amplifiers may include the Behringer NX3000 amplifier for this operating range (Behringer Amplifiers, MusicTribe Inc., Las Vegas, NV).

In some embodiments, inductor coil pickup sensors are affixed to the cylinder casing of each LFE transducer. Since the piston is a magnet, the coil faithfully transduces piston movement to a signal for monitoring of the independent stereo drive patterns. The pickup coils are connected to a multichannel sound amplifier with USB interface for real time plotting and tracking of use of the seat. An exemplary analog to digital converter amplifier may include the Focusrite 18i20 analog-digital converter amplifier combination which interfaces to a PC computer (Focusrite Inc, High Wycombe, Great Britain). The signal may be displayed by software rendering in standard oscilloscope tracings as well as surround sound depiction to capture interferential beat effect traversal in the body. An exemplary software may include the Virtins Multi-instrument software for oscilloscope rendering (Virtins Technology, Singapore) and the MasterPinguin Surround Sound software for surround depiction of the body in a coronal plane (Pinguin Ingineurbuero GmBH, Hamburg, Germany). The signals may be super-imposed in the subject to generate a super-imposed signal (e.g. a beat signal).

Modifications to these embodiments by use of alternative transducer and sensor types, methods of subject beat frequency generation, and bed design may be familiar to those skilled in the art. All are within the spirit and scope of these claims.

EXAMPLES

Human Subjects

Human subjects approval for this study was received from the Institutional Review Board (IRB) at Brigham Young University (IRB #: F19226). Written informed consent was received from all subjects. Participants were compensated for completion of the four sessions and surveys.

Inclusion criteria were designed to maximize the potential for decrease in sleep latency due to vibration treatment. The selected subjects had self-reported poor sleep with at least mild insomnia symptoms on the Insomnia Severity Index (ISI >7). Subjects were excluded if they had clinically diagnosed sleep disorders such as shift work sleep disorder, sleep apnea, and circadian sleep disorders. For safety concerns, subjects were also screened and excluded if they had a history of neck pain, diseases of the cervical spine or musculoskeletal disorders. To reduce the amount of possible confounding variables, subjects were also screened and excluded for illicit drug, alcohol, and excessive caffeine use, as these have been shown to affect sleep.

Beat Frequency Vibration Bed System

Figure 5A:
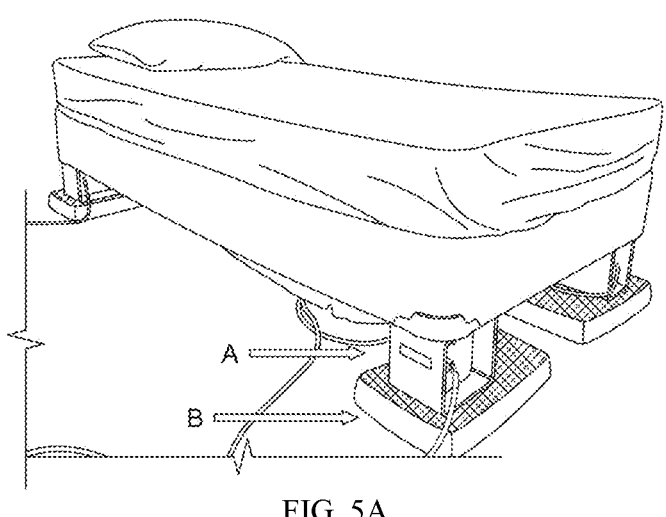
FIG. 5A illustrates an embodiment of a bed vibrating system where an independently driven mounted vibration transducer is positioned under each corner of the box spring.
Figure 5B:
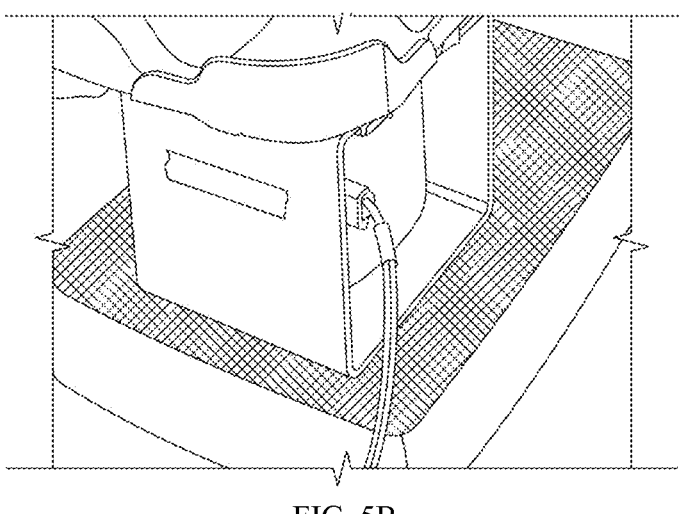
FIG. 5B shows isolation pads placed underneath each vibration mount to reduce noise and prevent the propagation of mechanical vibrations to the ground.

A novel dual frequency bed vibration system was created for use in this study. The system consisted of four custom steel mounts containing ButtKicker® Concert vibration transducers. These vibrating mounts (A) were placed under each corner of the box spring of a twin sized bed (see FIGS. 5A and 5B). A foam pad (B) was also placed underneath the transducer (A). The signals for each transducer were produced by a Rigol DG812 dual channel waveform generator, and the signals were amplified using XTi series Crown amplifiers. Two frequency combinations were used in this study. First, all four transducers were driven at 26.75 Hz. This combination will be referred to as standing wave vibration (SWV). The second combination was produced by driving one half of the bed (divided laterally) at 26.5 Hz, and the other half at 27 Hz. This combination results in a 0.5 Hz beat frequency and will be referred to as beat frequency vibration (BFV).

Figure 6A:
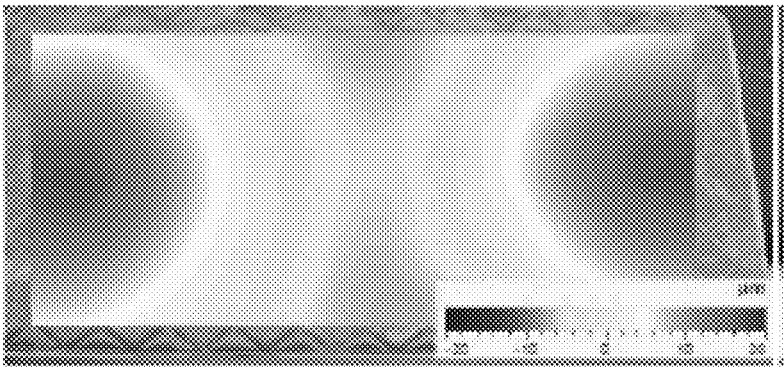
FIG. 6A shows an operating deflection shape of the bed vibrating at 15 Hz.
Figure 6B:
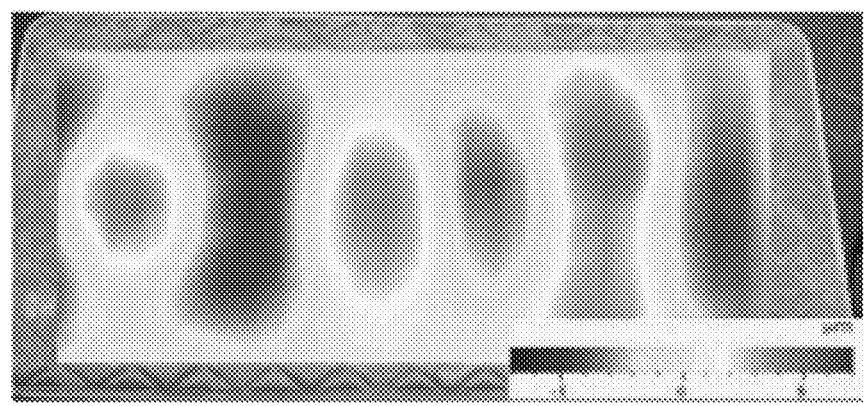
FIG. 6B shows an operating deflection shape of the bed vibrating at 27 Hz.

When vibrating the bed with the four actuators, different vibration patterns known as operating deflection shapes (ODSs) develop at different frequencies. In this study, we used a Polytec PSV-500-3D scanning laser Doppler vibrometer to measure the frequency response and determine the ODSs of the bed. We found that the largest response for the system occurred at 15 Hz with comparably high responses at 21 Hz and 27 Hz. The spatial vibration response of the bed when all four vibration drivers were vibrating at 15 Hz is shown in FIG. 6A. While 15 Hz elicited the highest response, the ODS of the bed at this frequency primarily targets the head and foot of the bed, while producing a smaller reaction in the middle of the bed. With all four drives vibrating at 27 Hz, the ODS targets the entire bed (see FIG. 6B). Therefore, we used standing wave and beat frequency combinations near 27 Hz. We believe that oscillations of 2 Hz and lower are generally most effective at inducing/improving sleep, therefore, we selected a beat frequency somewhere in this range for further clinical testing.

Recording Characteristics and Instrumentation

The bed vibration system was placed in a sound isolation chamber (Industrial Acoustics, double wall) that exceeded standards for audiometric testing as set forth by the American National Standards Institute. Participants were asked to lay in the bed, close their eyes, and sleep if possible. Each participant did this for up to two hours, or until they woke up from a nap and did not feel that they would fall asleep again. This process was repeated over the course of four sessions. Brain activity was measured using the Compumedics Neuroscan high-density electroencephalography (HD-EEG) system with the SynAmpsRT 64-channel amplifier and recorded using the EEG software: Curry 7©. A sampling rate of 1 kHz was used during recording.

Figure 7:
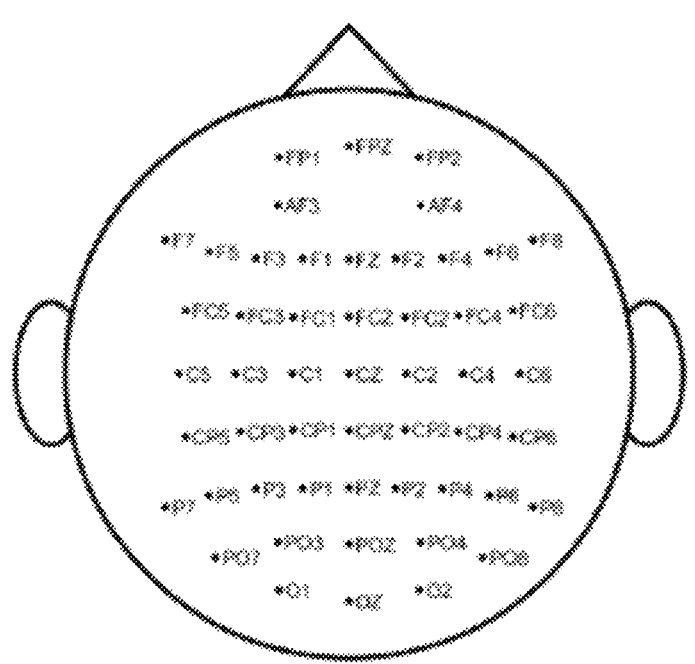
FIG. 7 shows locations of HD-EEG cranial electrodes that were used for analysis.

A 64-channel Quick-Cap with 4 integrated bipolar leads for vertical and horizontal EOG (VEOG, HEOG), EMG, and EKG were used. Brain activity was recorded with sintered Ag/AgCl electrodes (Compumedics Neuroscan EEG, Charlotte, NC) with the SynAmpsRT 64-channel amplifier and recorded with the EEG software: Curry 7©. The electrode placement follows the internationally accepted 10-20 placement system of the sensor net's electrodes (electrodes are placed at 10% and 20% along lines of latitude and longitude). A common average reference automatically calculated by Curry 7© was used. FIG. 7 shows the locations of the 52 cranial electrodes that were used during analysis. Some of the electrodes in the temporal region were excluded because they were found to be more prone to noise during vibration testing.

Testing Procedure

Participants were given identification numbers, and all data were stripped of unique identifiers. To prevent any placebo effect, participants were not told the hypothesis of this study.

Throughout, the participants were required to fill out a sleep diary every morning and evening. The sleep diary contained questions about the participant's sleep patterns and the activities that they performed throughout the day. This allowed for tracking of general sleep patterns and identification of potential confounding variables. Participants were required to come to four in-lab sessions. Each of these sessions was separated by one week.

The first in-lab session was a habituation session in which participants were acclimated to sleeping in the lab's bed with the cap on. The next three sessions had one of three conditions applied: control, SWV, or BFV. The control session was always third, and the two vibration conditions were randomly assigned to be the second or fourth session for each participant. During the control session, the vibrating mounts were removed from under the bed and placed on vibration isolation pads so that no mechanical vibration would be transferred to the participant, but they were still turned on to achieve the same noise level as during the vibration sessions.

To select the exact frequency and amplitude combinations for the two vibration sessions, participants were recruited to lay in the vibrating bed for a few minutes and subjectively rate the comfort appeal of the system as the vibration frequencies and amplitudes were adjusted. This was done on a separate occasion prior to the test sessions previously described. It was found that most participants preferred a beat frequency of 0.5 Hz, and a peak acceleration of 0.2 m/s² RMS. This amplitude is comparable to other studies that investigate the effect of vibration on sleep, as they typically use 0.2 to 0.3 m/s² RMS. Because of this, the bed was driven with a peak acceleration of 0.2 m/s² RMS for all participants during both vibration sessions.

During the SWV session, the vibrating mounts were all driven at 26.75 Hz. During the beat frequency session, one half of the bed (divided laterally) was driven at 26.5 Hz, and the other was driven at 27 Hz. This combination led to a 0.5 Hz horizontal traveling wave that propagated left-to-right across the user's entire body.

The in-lab sessions took place in the afternoon at the same time of day across all four sessions. After the vibration sessions, participants were asked to subjectively rate their experience using a Likert scale survey. They were asked about the comfort of the system, whether or not the vibration helped them to fall asleep faster, whether it improved the quality of their sleep, and whether or not they would prefer to use it over an entire night of sleep.

HD-EEG Data Processing

The HD-EEG data were visually scored with Curry 7© using 30-second epochs according to the sleep staging rules of the AASM scoring manual criteria [33]. To remove artifacts from the bed vibration system and any other sources of interference, all data were filtered using a Hann filter (FFT-type filter). The filter types used included a high pass filter set at 1 Hz and a low pass filter set at 30 Hz, as well as a band-stop filter centered at 26.75 Hz with a width of 4.0 Hz and a slope of 1 Hz. These values were selected to remove any effects from the vibration transducers and the 0.5 Hz traveling wave. Additional artifact removal was performed using the MATLAB toolbox EEGLAB. Artifacts were defined as any occurrence of HD-EEG activity caused by external events such as eye blinks or other movement. All naturally occurring events such as k-complexes and sleep spindles were included in the analyses.

Multi Scale Sample Entropy

Conscious awareness may be quantified by the complexity or entropy of the HD-EEG waveform. Entropy quantifies the irregularity of time series data signals. Entropy is lower for predictable signals (such as a regular sine wave), and higher for signals with low predictability. In this study, multi-scale sample entropy (MSE) was used as a measure of complexity. MSE was chosen because physiological systems are characterized by varying waveforms, the complexity of which is best characterized over various time scales.

MSE is a variation of sample entropy (SampEn), a time-series analysis method. A full technical description for calculating MSE will not be described herein, but Costa et al. provides a detailed explanation of this process (Costa, M.; Goldberger, A. L.; and Peng, C. K. "Multiscale Entropy Analysis" PhysioNet).

In this study, SampEn was calculated using run length $m=2$ and tolerance window $r=0.15*SD$ (standard deviation), as this has been shown to be acceptable. To produce a quantifiable value to represent the MSE for a given time series, the values from timescale $t=20$ to $T=30$ were averaged. This method for quantifying MSE was determined acceptable for this study because the SampEn vs. time scale plots level off around 20, and taking the average helps decrease the effects of outlying values at any given time scale.

Analysis

Sleep Latency. One metric obtained from the filtered HD-EEG data was sleep latency. Two definitions of sleep latency were used. The first definition is the AASM standard defined as the amount of time from lights off to the first occurrence of a 30 second epoch classified as non-wakefulness. The second definition was the amount of time from lights off to the first 30 second epoch classified as non-wakefulness followed by at least two minutes of continued sleep. This will be referred to as unequivocal sleep. A similar definition of unequivocal sleep was used in which 3 continuous epochs of stage N1 sleep were required.

MSE Validation. To verify the effectiveness of MSE for tracking changes in brain activity, the average MSE values were compared between wake, N1 sleep, and N2 sleep. This was done by taking the average control session data for all participants and plotting the MSE values on a topographic HD-EEG head plot for the three sleep-wake states mentioned.

MSE Analysis. Average MSE values during wake, N1 sleep, and N2 sleep were calculated during each session and then plotted on topographic HD-EEG plots. The results from the standing wave and BFV sessions were then compared per electrode to the control session to determine the effects that vibration type has on neural complexity.

Power Spectral Density Analysis. Power spectral density (PSD) analysis was performed on the EEG data to determine the effect of vibration on the expression of sleep and wake drive. A Fast Fourier Transform (FFT) was performed for every five second window of EEG data per electrode. It was desired to track the power spectrum of the different brain wave types over the course of the testing session. Brain wave frequency ranges were defined as delta 0-3.99 Hz, theta 4-7.99 Hz, alpha 8-13 Hz, and beta greater than 13 Hz. To account for natural fluctuations in brain activity and differences between subjects, relative PSD values were used, meaning the PSD value for a given frequency range divided by the sum total PSD of all four frequency ranges. Alpha rhythms are more prominent during wakefulness and are strengthened during tasks requiring mental arithmetic and visual imagery. Therefore, relative alpha PSD will be used as a measure of the expression of arousal (or wake drive). Additionally, relative delta PSD was used as a measure of the expression of sleep drive, as delta waves are typical during deeper stages of NREM sleep.

Subjective Ratings. A subjective questionnaire was given to participants after the sessions. The results were used to analyze user preferences between the two vibration types.

Statistical Analysis. All statistical analyses were performed, and p-values obtained using a linear, mixed models analyzing variance with blocking on subjects. We performed post-hoc pairwise t-tests to determine where there were differences between treatments. This analysis is appropriate due to the expected deviation in baseline sleep characteristics between subjects. The variance was estimated using the restricted maximum likelihood (REML) approach. Significance was determined at the $p \leq 0.05$ level, except where otherwise specified in the results section. For example, some values at the $p \leq 0.1$ were considered in the Multi Scale Sample Entropy section. Analyses were performed using JMP (v14).

Participants

For this study, 14 college students (8 female, 6 male, mean age $22.2 \pm 3.0$) were recruited. Table 1 shows the demographic and sleep features of the sample population. Most participants have self-reported, clinical insomnia of moderate severity according to the ISI. Participants had an average self-reported sleep latency of over 40 minutes with high variability during the study period.

TABLE 1

| Participant Demographic Table | |
| --- | --- |
| Gender | 6 male |
| | 8 female |
| Age | $22.2 \pm 3.0$ years |
| Weight | $148.8 \pm 22.3$ lbs. |
| Height | $67.6 \pm 2.8$ inches |
| Race/Ethnicity | White - 10 participants |
| | Hispanic/Latino - 1 participant |
| | Native Hwaiian - 1 participant |
| | Asian - 1 participant |
| | Mixed - 1 participant |
| Average sleep latency during period of study | $41.1 \pm 28.4$ minutes |
| ISI scare | $15.1 \pm 3.7$ |
| Education | All participants were undergraduate college students |

Data from three participants were excluded due to non-related factors. The first was excluded due to ending two sessions early to use the bathroom. The second was excluded due to not having slept the night before a session. The 3rd was excluded due to self-report in the diary of a menstruation period which reportedly greatly affected sleep during the final session.

B. Sleep Latency and Sleep Stages

Figure 8:
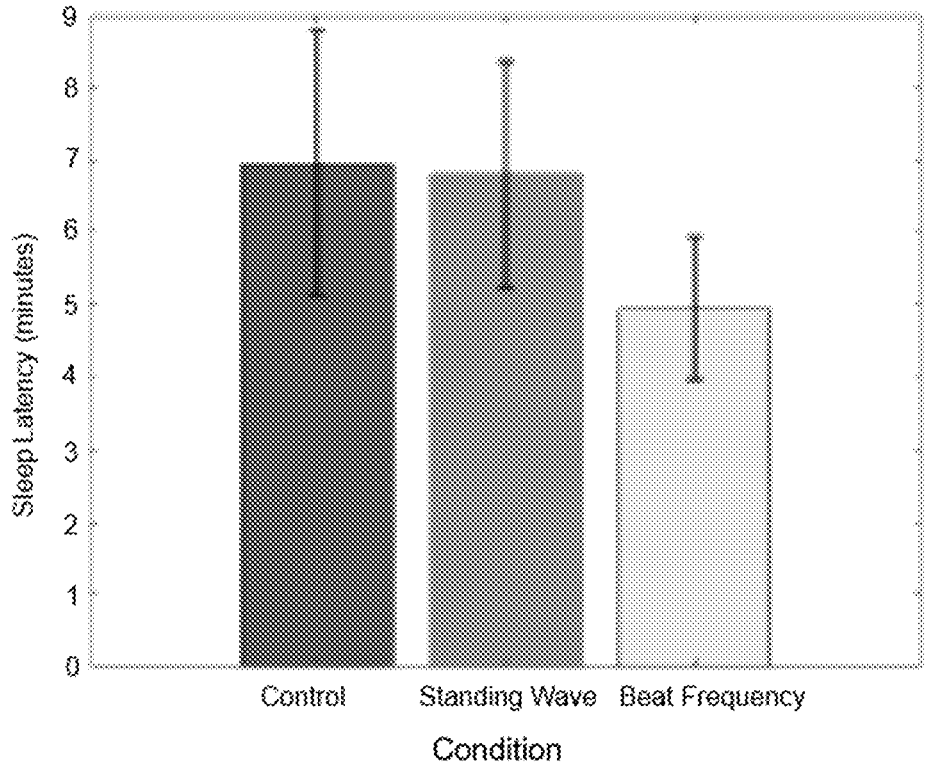
FIG. 8 shows mean AASM sleep latency in minutes for each of the three conditions. The error bars show the standard error for each condition. For the control group, the average sleep latency in minutes was 6.95±1.83 (mean±SEM), for the SWV session it was 6.80±1.56 (mean±SEM), and for the BFV session it was 4.94±0.99 (mean±SEM).

The average AASM sleep latencies for each condition are shown in FIG. 8. The variance (in minutes$^2$) for the control, SWV, and BFV sessions are 36.7, 26.9, and 10.7, respectively.

Figure 9:
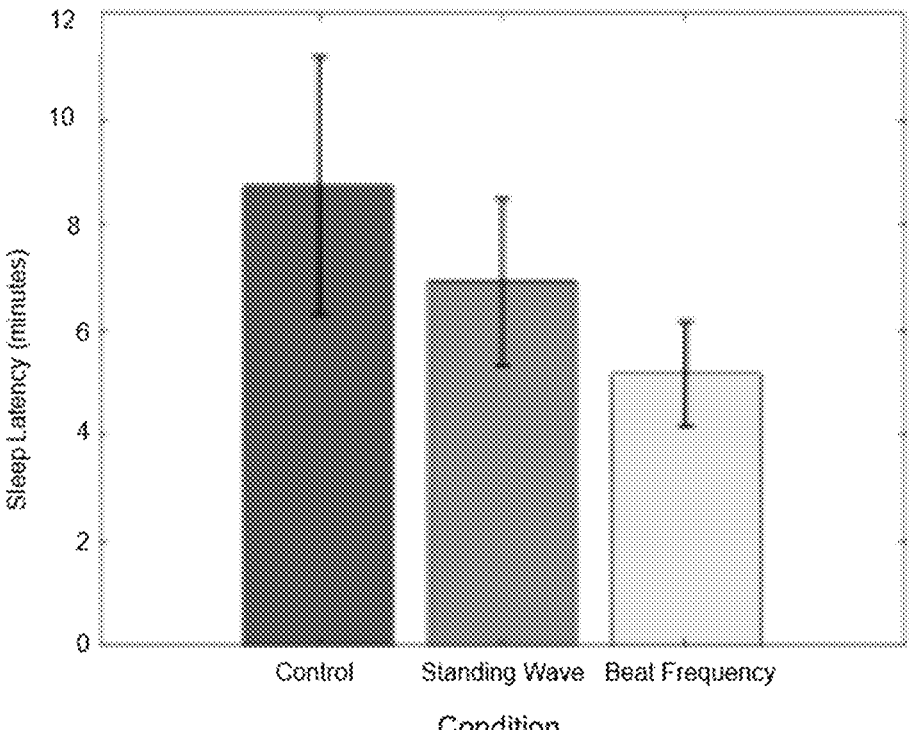
FIG. 9 shows mean unequivocal sleep latency in minutes for each of the three conditions. The error bars show the standard error for each condition. For the control group the average sleep latency in minutes was 8.73±2.43 (mean±SEM), for the SWV session it was 6.92±1.59 (mean±SEM), and for the BFV session it was 5.18±1.00 (mean±SEM).

The average unequivocal sleep latencies are shown in FIG. 9. The variance (minutes$^2$) for the control, SWV, and BFV sessions were 64.8, 27.9, and 11.0, respectively.

Statistical analysis as described in the analysis section determined if there was a difference in means between the three conditions. Table 2 shows the two tailed p-values and the upper and lower bounds for 95% confidence intervals comparing the two vibration sessions to the control session.

TABLE 2

| | Sleep Latency P-values | |
|---|---|---|
| Sleep Latency Definition | Standing Wave Vibration | Beat Frequency Vibration |
| AASM $F_{2,20} = 1.87$, p = 0.33 | $p \leq 0.915$ Upper CL = 3.197 Lower CL = -2.882 | $p \leq 0.181$ Upper CL = 5.058 Lower CL = -1.022 |
| Unequivocal Sleep ($F_{2,20} = 1.87$, p = 0.18) | $p \leq 0.336$ Upper CL = 5.657 Lower CL = -2.024 | $p \leq 0.068$ Upper CL = 7.399 Lower CL = -0.281 |

Two tailed P-values were calculated for determining whether there was a difference between the mean sleep latency during the control session and the two vibration sessions. The 95% confidence interval upper and lower bounds for the difference between the control and vibration sessions are also reported. For example, the BFV upper bound for AASM latency suggests that BFV caused participants to fall asleep 5.058 minutes faster than during the control session. The F-value in the table is for the overall test for differences between treatments. Table 3 shows the percentage of each sleep state during the first hour for each condition.

TABLE 3

| | Wake-Sleep State Percentages | | | |
|---|---|---|---|---|
| Condition | Wake | N1 | N2 | N3 |
| Control | 19.5 | 27.3 | 44.2 | 8.9 |
| Standing Wave Vibration | 34.1 | 29.3 | 32.6 | 4.4 |
| Beat Frequency Vibration | 22.3 | 30.4 | 39.5 | 7.7 |

Based on a power analysis of the observed differences, a sample size of 24 would be required to achieve significance in unequivocal sleep latency difference for the comparison of BFV treatment to the control. The same comparison would require a sample size of 46 for the AASM definition. Differences between SWV treatment and the control were small, indicating that a larger sample may not result in meaningful significance by either definition of sleep latency.
Multi Scale Sample Entropy Validation Results The control session MSE values during the first minutes of wake, N1, and N2 sleep stages were averaged for all participants. MSE drops in 44 of the 52 electrodes when transitioning from wake to N1 sleep, but the difference is not statistically significant. MSE then drops again significantly from N1 to N2 sleep. The difference in MSE between wake and N2 is statistically significant with $p \leq 0.002$ for all electrodes. This shows that neural complexity drops significantly when transitioning from wake to N2.
Multi Scale Sample Entropy Results The MSE topographical HD-EEG plot comparisons for wake, N1, and N2 stages were completed. MSE values were averaged across all participants. Analysis was performed on the first two minutes of each sleep stage, excluding any artifacts. Analysis of N3 sleep was not included because too few participants entered this stage of sleep.

The color scales used are relative to the stage of sleep being analyzed. This means that the color scales are different for each stage of sleep but are the same between sessions within their respective sleep stage. This allows for observation of subtle differences in MSE between conditions for each sleep stage. Therefore, the color scales between sleep stages should be noted. For example, the MSE scale during N2 sleep (1.78 to 1.98) is significantly lower than the MSE values during wake and N1 sleep (2 to 2.18 and 2 to 2.16 respectively).

Upon observation, it can be seen that overall MSE dropped slightly from wake to N1 sleep and dropped significantly from N1 to N2 sleep. Wake MSE is generally lower in the frontal regions during both vibration conditions than during the control, and MSE is lower during the BFV condition in the medial parietal region than the other conditions. Stage N1 sleep MSE is generally higher during BFV, although electrode CPZ is still notably lower than the other two regions. Stage N2 sleep MSE is generally higher during the control session throughout the entire central region than both of the vibration conditions.

Table 4 shows the electrodes that underwent a significant change between the control session and the two vibration treatment sessions. P-values were obtained using a linear mixed models analysis of variance with blocking on subjects as described previously. In Table 4, both electrodes which are significant at the $p \leq 0.05$ level (bolded) and significant at the $p \leq 0.1$ level (non-bolded) are shown. It was determined that significance at the $p \leq 0.1$ level would also be considered due to the fact that this is a pilot study, and while significance at the $p \leq 0.1$ is not conclusive, it is suggestive of a trend. Based on a power analysis of the observed differences, a sample size of 30 would be required to achieve statistical significance for all non-significant electrodes ($p \geq 0.05$) shown in Table 4.

TABLE 4

| | Electrodes with Significant Changes in MSE | | | |
|---|---|---|---|---|
| Sleep Stage | Standing Wave Vibration | | Beat Frequency Vibration | |
| | Higher MSE | Lower MSE | Higher MSE | Lower MSE |
| Wake $F_{2,20} = 1.92$, p = 0.17 | CP5 $p \leq 0.034$ P7 $p \leq 0.031$ O2 $p \leq 0.038$ PO7 $p \leq 0.023$ PO4 $p \leq 0.009$ PO8 $p \leq 0.044$ CP4 $p \leq 0.080$ O1 $p \leq 0.084$ | AF4 $p \leq 0.008$ C1 $p \leq 0.040$ FP2 $p \leq 0.065$ FC4 $p \leq 0.080$ | P7 $p \leq 0.024$ P8 $p \leq 0.059$ PO4 $p \leq 0.073$ | |
| N1 $F_{2,20} = 1.71$, p = 0.21 | | | P1 $p \leq 0.075$ | O2 $p \leq 0.097$ |
| N2 $F_{2,20} = 1.92$, p = 0.18 | | | | F7 $p \leq 0.041$ FP1 $p \leq 0.087$ FC5 $p \leq 0.095$ CP3 $p \leq 0.056$ O1 $p \leq 0.077$ AF3 $p \leq 0.084$ F5 $p \leq 0.065$ |

Figure 10:
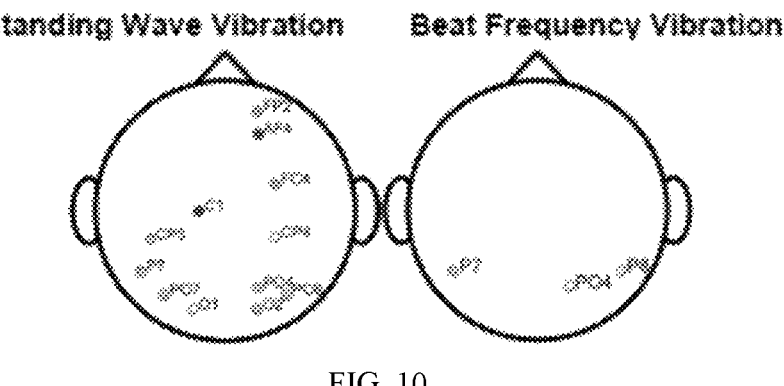
FIG. 10 shows electrodes which differ in MSE significantly during wake from the control session in the SWV session (left) and BFV session (right). Yellow electrodes indicate increased MSE, and blue electrodes indicate decreased MSE. Darker colors are significant at the p≤0.05 level, and light colors are significant at the p≤0.1 level.

During the wake stage, 29 of the 52 electrodes analyzed showed an average decrease in MSE during the SWV session, and 27 of the 52 electrodes showed an average decrease in MSE during BFV session. MSE significantly increased in eight electrodes and decreased in four electrodes during the SWV session. MSE significantly increased in three electrodes during the BFV session (see Table 4). FIG. 10 shows a plot of the electrodes which underwent a statistically significant change for the two vibration conditions. In general, decreases in MSE during this stage occurred in the parietal region, while increases occurred in the frontal region.

Figure 11:
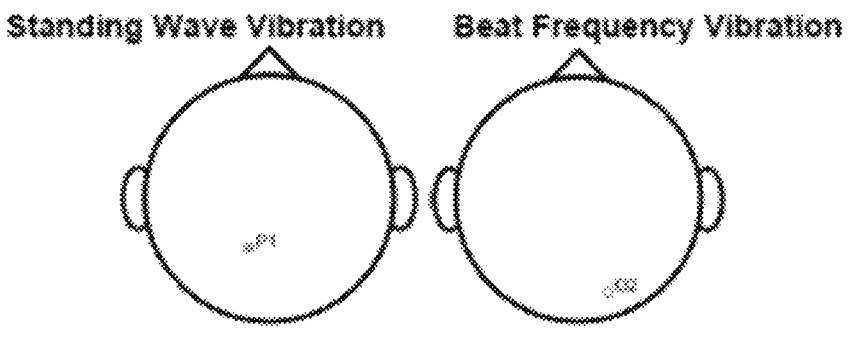
FIG. 11 shows electrodes which differ in MSE significantly during N1 sleep from the control session in the SWV session (left) and BFV session (right). Yellow electrodes indicate increased MSE, and blue electrodes indicate decreased MSE. Darker colors are significant at the p≤0.05 level, and light colors are significant at the p≤0.1 level.

During stage N1 sleep, 40 of the 52 electrodes analyzed showed an average decrease in MSE during the SWV session, and 1 of the 52 electrodes showed an average decrease in MSE during BFV. One electrode was found to decrease in MSE during SWV, and one electrode increased in MSE during BFV (see FIG. 11). Due to a general lack of significance, differences between sessions may be due to outlying data.

Figure 12:
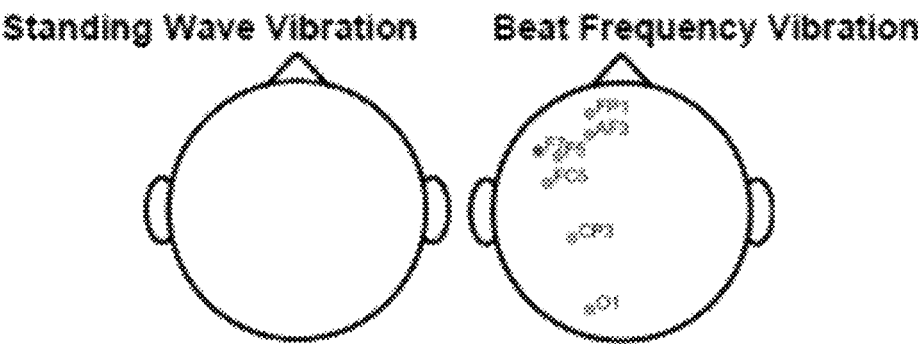
FIG. 12 shows electrodes which differ in MSE significantly during N2 sleep from the control session in the SWV session (left) and BFV session (right). Yellow electrodes indicate increased MSE, and blue electrodes indicate decreased MSE. Darker colors are significant at the p≤0.05 level, and light colors are significant at the p≤0.1 level.

During the stage N2 sleep, 49 of the 52 electrodes analyzed had a lower average MSE during SWV than during the control session, and 47 of the 52 electrodes had a lower average MSE during the beat frequency session than during the control session. MSE did not significantly change in any of the electrodes during the SWV session. MSE significantly decreased in seven electrodes during the BFV session which can be seen in FIG. 12. All seven of these electrodes were in the left hemisphere of the brain.

Power Spectral Density Results

The relative beta, alpha, theta, and delta PSD during the first two minutes of wake, N1, and N2 sleep were compared. For all conditions, the PSD results followed typical trends such as higher occurrence of beta waves during wake, higher alpha during wake (especially in the parietal regions) and increasing theta and delta waves as participants went deeper into sleep.

SWV was shown to significantly decrease alpha rhythms in frontal and central regions and increase delta rhythms throughout much of the frontal and left central and parietal regions during wake. BFV was shown to increase delta rhythms in the left frontal region during stage N2 sleep. The electrodes affected and their corresponding p-values are shown in Tables 5 to 8.

TABLE 5

Relative Beta PSD Changes

| Sleep Stage | Standing Wave Vibration | | Beat Frequency Vibration | |
|---|---|---|---|---|
| | Higher PSD | Lower PSD | Higher PSD | Lower PSD |
| Wake | P4 ≤0.006 PO6 ≤0.026 PO8 ≤0.006 | | P2 ≤0.048 P4 ≤0.019 PO4 ≤0.046 PO6 ≤0.030 | O1 ≤0.032 |
| N1 | | | CP4 ≤.050 PZ ≤.046 PO4 ≤0.034 | |
| N2 | | | | |

TABLE 6

Relative Alpha PSD Changes

| Sleep Stage | Standing Wave Vibration | | Beat Frequency Vibration | |
|---|---|---|---|---|
| | Higher PSD | Lower PSD | Higher PSD | Lower PSD |
| Wake | | FP2 ≤0.041 AF4 ≤0.032 F5 ≤0.013 FCZ ≤0.043 C2 ≤0.049 C4 ≤0.027 | | |

TABLE 6-continued

Relative Alpha PSD Changes

| Sleep Stage | Standing Wave Vibration | | Beat Frequency Vibration | |
|---|---|---|---|---|
| | Higher PSD | Lower PSD | Higher PSD | Lower PSD |
| | | CP5 ≤0.037 CP3 ≤0.046 CP2 ≤0.009 | | |
| N1 | | | | |
| N2 | CP4 ≤0.047 | | CP4 ≤0.047 | |

TABLE 7

Relative Theta PSD Changes

| Sleep Stage | Standing Wave Vibration | | Beat Frequency Vibration | |
|---|---|---|---|---|
| | Higher PSD | Lower PSD | Higher PSD | Lower PSD |
| Wake | | | | |
| N1 | | | | FZ ≤0.042 F6 ≤0.024 F8 ≤0.027 FC1 ≤0.027 FCZ ≤0.008 FC6 ≤0.036 C1 ≤0.041 CZ ≤0.014 CP1 ≤0.016 P3 ≤0.048 P1 ≤0.040 PZ ≤0.024 P2 ≤0.045 PO3 ≤0.033 POZ ≤0.0272 PO4 ≤0.048 OZ ≤0.047 O2 ≤0.033 |
| N2 | | FC6 ≤0.040 C3 ≤0.024 C4 ≤0.040 CP5 ≤0.014 CP3 ≤0.013 CP1 ≤0.007 CP2 ≤0.016 CP6 ≤0.017 P7 ≤0.023 P5 ≤0.028 P3 ≤0.023 P1 ≤0.034 P2 ≤0.028 P6 ≤0.031 P8 ≤0.042 PO7 ≤0.033 PO5 ≤0.037 PO8 ≤0.034 OZ ≤0.031 | | FC6 ≤0.037 C5 ≤0.038 CP5 ≤0.020 CP3 ≤0.033 CP1 ≤0.005 CP2 ≤0.017 CP6 ≤0.022 P7 ≤0.018 P5 ≤0.034 P2 ≤0.017 P4 ≤0.034 P6 ≤0.022 P8 ≤0.038 PO5 ≤0.045 PO6 ≤0.042 PO8 ≤0.017 OZ ≤0.045 |

TABLE 8

Relative Delta PSD Changes

| Sleep Stage | Standing Wave Vibration | | Beat Frequency Vibration | |
|---|---|---|---|---|
| | Higher PSD | Lower PSD | Higher PSD | Lower PSD |
| Wake | FPZ ≤0.020 FP2 ≤0.014 AF3 ≤0.025 AF4 ≤0.012 F7 ≤0.020 F5 ≤0.004 F3 ≤0.021 F1 ≤0.035 | | | |

TABLE 8-continued

| | Relative Delta PSD Changes | | | |
|---|---|---|---|---|
| Sleep | Standing Wave Vibration | | Beat Frequency Vibration | |
| Stage | Higher PSD | Lower PSD | Higher PSD | Lower PSD |
| | FZ ≤0.031 | | | |
| | F2 ≤0.012 | | | |
| | F4 ≤0.008 | | | |
| | F6 ≤0.004 | | | |
| | F8 ≤0.010 | | | |
| | FC5 ≤0.014 | | | |
| | FC3 ≤0.097 | | | |
| | FCZ ≤0.034 | | | |
| | FC6 ≤0.018 | | | |
| | C5 ≤0.007 | | | |
| | C3 ≤0.015 | | | |
| | C1 ≤0.009 | | | |
| | C4 ≤0.022 | | | |
| | CP5 ≤0.007 | | | |
| | CP3 ≤0.031 | | | |
| | CP2 ≤0.013 | | | |
| | P7 ≤0.011 | | | |
| | P5 ≤0.019 | | | |
| | P3 ≤0.017 | | | |
| | PO7 ≤0.012 | | | |
| | PO3 ≤0.043 | | | |
| N1 | | | | |
| N2 | | | FP1 ≤0.046 | |
| | | | FPZ ≤0.018 | |
| | | | F7 ≤0.047 | |
| | | | F5 ≤0.036 | |
| | | | CP2 ≤0.039 | |

Subjective Ratings Results

Table 9 contains the results of the Likert scale questions given to participants after the vibration sessions. These questions focused on the comfort of the vibration and whether it caused a faster transition to sleep or higher quality of sleep. On average, participants rated the BFV session as being more comfortable, helping them to fall asleep faster, and improving the quality of their sleep during the entire sleep session. However, these differences were not statistically significant.

TABLE 9

| | Subjective Rating Results | | | |
|---|---|---|---|---|
| Condition | The vibration was comfortable | The vibration helped me to fall asleep faster | The vibration improved the quality of my sleep during the entire sleep session | I would prefer not to use it over an entire night of sleep |
| Standing Wave Vibration | 3.786 | 3.000 | 2.714 | 2.357 |
| Beat Frequency Vibration | 4.000 | 3.071 | 3.143 | 2.500 |

Discussion

In this study we aimed to show that BFV-induced by superimposing two different vibration waves could be a plausible non-pharmacological treatment for individuals with poor sleep. We compared the effect that BFV of 0.5 Hz and traditional SWV have on different physiologic and subjective metrics. Statistically significant results as well as trends are discussed for each metric in the following sections.

Sleep Latency

Sleep latency results are suggestive of a modest decrease in the amount of time that it took participants to fall asleep when subjected to the BFV session. In particular, the unequivocal sleep latency results are indicative of this trend. Between the two definitions of sleep latency, unequivocal sleep may be considered more appropriate, as it represents the amount of time for a person to achieve lasting sleep, which is the goal.

In addition to having a lower mean than the control and SWV sessions, the BFV session had a much lower variance. This implies that BFV may produce more consistently low sleep latency times with fewer outliers.

Sleep latency (by both definitions) was relatively low (average of less than 10 minutes) for all sessions. This was somewhat unexpected when considering that participants were recruited from a population of persons having moderate to severe self-reported insomnia. This may in part be explained by the fact that testing took place in the early afternoon, which is known to be a time when sleep drive peaks. Regardless of the cause, the generally low sleep latencies result in a floor effect, which can complicate the process of identifying strong statistical evidence of a difference between groups.

Multi Scale Sample Entropy Validation

MSE during N2 sleep was shown to be significantly lower than during wake and N1 sleep. MSE values were lower during N1 than during wake, but not significantly. In some cases, wake and N1 may have nearly the same value of MSE. This shows that MSE is an effective tool for quantifying changes in neural complexity as a person transitions from wake to deeper stages of sleep. Because deeper stages of sleep such as N2 are associated with lower brain activity, it stands to reason that MSE may be used to represent a person's conscious awareness. Conscious awareness impacts a person's sleep-wake state.

Multi Scale Sample Entropy

During the wake stage, it was found that for both vibration conditions, nearly half of the electrodes had a higher average MSE, and nearly half had lower MSE. In general, the decreases in MSE occurred in the frontal regions, and the decreases occurred in the parietal and occipital regions. This discrepancy between the frontal and parietal/occipital regions is likely due to the fact that alpha waves, which are common during resting wake, occur predominantly in the parietal/occipital regions of the brain. Because SWV shows decreased MSE in some frontal regions, there is some cause to believe that this may decrease conscious awareness during wake. The electrodes, however, do not line up well with regions that have been shown to be associated with conscious awareness. It is, therefore, difficult to conclude significant changes in conscious awareness during the wake stage.

During N1 sleep, there were no electrodes which demonstrated a significant change in MSE at the $p \leq 0.05$ level, and only two showed a significant change at the $p \leq 0.1$ level (between both vibration conditions). This makes it difficult to conclude the effects that either type of vibration may have on MSE during N1 sleep.

During N2 sleep, most electrodes showed a decrease in MSE during both vibration conditions. Only the BFV condition, however, caused a significant difference. All significant electrodes are in the left hemisphere of the brain (FIG. 14). One possible explanation for this is because insomnia has been linked to altered glucose metabolism in left frontoparietal heteromodal cortices that show smaller NREM sleep-wake differences in these areas. The significant frontal electrodes (FP1, AF3, F7, F5, and FC5) and CP3 map into this frontoparietal area. This could mean that BFV is able to counteract the disruptive processes that impede healthy NREM activity in individuals with poor sleep. Additionally, neuroimaging studies have shown that conscious awareness may be associated with brain activity in the left middle frontal gyrus. Electrodes FC5 and F5 lie in this region, which indicates that BFV may lead to reduced conscious awareness during deeper stages of sleep.

Power Spectral Density

While there were multiple HD-EEG electrodes that underwent significant changes in each frequency band, the alpha and delta bands were of most interest due to their use as measures for expression of arousal and sleep drive respectively. During wake, SWV lowered the relative alpha PSD in the central and frontal regions and increased relative delta PSD throughout most of the left and frontal regions of the brain. This suggests that during wake, SWV may reduce the expression of arousal, as well as increase the expression of sleep drive. These changes do not manifest during sleep, implying that these benefits do not persist.

BFV was shown to increase relative delta PSD during stage N2 sleep, that suggests that this treatment may increase sleep drive expression during deeper stages of sleep. This finding is consistent with the MSE findings, in which BFV was shown to reduce neural complexity. This adds to the hypothesis that BFV may be of benefit to those who suffer from poor sleep quality, particularly in deeper stages of sleep.

These PSD results indicate that SWV may cause faster transition into sleep (although this is not supported by the sleep latency results), and that beat frequency may produce more benefits during N2 sleep. This implies that the use of different vibration types may be appropriate based on a given patient's needs and their current sleep-wake state.

Subjective Ratings

Participants generally found both vibration types to be comfortable and reported that it may improve their sleep. There was a slight inclination towards BFV over SWV, although more participants would be needed to show significance.

In this study BFV demonstrated a trend towards decreasing sleep latency, particularly when defined as achieving unequivocal sleep. BFV also shows more consistently low latencies with fewer outliers than the control and SWV conditions.

Because the underlying frequency of the BFV was 26.75 Hz (the same frequency used for the SWV session), it was inferred that the difference in outcome between the SWV and BFV conditions is due to the presence of the 0.5 Hz traveling wave.

MSE was shown to be effective at quantifying the difference in neural complexity between wake and deeper stages of sleep and shows a general decrease in complexity between wake and N1 sleep. Both standing wave and BFV caused changes in all sleep-wake states that were analyzed, although primarily during wake and N2. SWV may decrease complexity in the frontal region, while both standing wave and beat frequency may cause increased complexity in the parietal/occipital regions. Varied MSE values and locations of significant electrodes during wake and N1 sleep make it difficult to conclude the effect on conscious awareness during these stages.

During N2 sleep, BFV led to reduced MSE in the left frontoparietal area of the brain. The location of some of these electrodes are known to relate to conscious awareness, and to show smaller NREM sleep-wake differences in individuals with poor sleep. This indicates that BFV may reduce conscious awareness in these individuals during deeper stages of sleep.

Based on changes in relative PSD, SWV may lead to decreased expression of arousal and increased sleep drive during wake, although these changes do not persist into sleep. BFV may cause higher expression of sleep drive during stage N2 sleep. This suggests that the use of different vibration types may be appropriate based on a given patient's needs and their current sleep-wake state.

In summary, our results suggest that BFV may help individuals with poor sleep by decreasing sleep latency, by reducing their conscious awareness, and by increasing sleep drive expression during deeper stages of sleep. SWV may be beneficial for decreasing expression of arousal and increasing expression of sleep drive during wake, implying that a dynamic vibration treatment may be beneficial.

The invention claimed is:

1. A system for introducing vibrational waves into a body of a subject, the system comprising:

a bed frame comprising a first vibration contact and a second vibration contact, the first vibration contact being in mechanical communication with a first location of the body of the subject, the second vibration contact being in mechanical communication with a second location of the body of the subject;

a first vibration source connected to the first vibration contact and configured to generate a first vibration of the first vibration contact;

a second vibration source connected to the second vibration contact and configured to generate a second vibration of the second vibration contact;

wherein a location and orientation of the first vibration contact and a location and orientation of the second vibration contact are configured in a manner that the first vibration combines with the second vibration to generate a super-imposed vibration;

a mouthguard sensor customized to the subject's maxillary tooth print pattern and positioned in mechanical contact with the subject to measure an amplitude and a frequency pattern of the super-imposed vibration; and wherein a derived waveform pattern from the mouth guard sensor demonstrates induced beat frequencies.

2. The system of claim 1, wherein the first vibration contact is a first panel positioned beneath a box spring or a mattress, and the second vibration contact is a second panel positioned beneath the box spring or the mattress.

3. The system of claim 2, wherein the first and second vibration sources are affixed to a respective undersurface of the first panel and the second panel to independently vibrate each of the first and second panels in a frequency range of 5 to 200 hertz (Hz), and transmit the vibrational waves to the subject that are combined by superposition in the subject.

4. The system of claim 2, wherein each of the panels is configured to be vibrated independently in a range of 5 to 200 hertz (Hz) with waveforms selected from arbitrary, sinusoidal, triangular, and rectangular waveforms with various duty cycles, or with a customized waveform shape and with sufficient power to induce subjective perception of vibration.

5. The system of claim 2, wherein each of the panels is configured to be vibrated at a same frequency with 0° to 180° of relative phase.

6. The system of claim 2, wherein each of the panels is configured to be vibrated at frequencies offset from each other in a manner as to induce an interferential beat frequency as a difference between two or more driving frequencies.

7. The system of claim 2, wherein each of the panels is configured to be vibrated independently with various waveforms in a range of 5 to 200 hertz (Hz) to induce beat frequencies in the range of 0.05 Hz to 200 Hz which can be perceived as traveling waves.

8. The system of claim 2, wherein each of the panels is configured to be vibrated independently to induce localized vibrational maxima into a subject's head, cervical spine, or both with phased inputs.

9. The system of claim 2, wherein each of the panels is configured to vibrate independently with sinusoidal waveform sources to induce vibration into the subject's body a range of 0.01 hertz (Hz) to 10 Hz.

10. The system of claim 2, wherein each of the panels is configured to vibrate independently to induce a harmonic from the vibrational waves into the subject's body in a range of 0.01 hertz (Hz) to 200 Hz.

11. The system of claim 2, wherein each of the panels is configured to have affixed to it or its attached low frequency effect (LFE) transducer a sensor from which an oscillatory signal is derived to monitor drive frequency and pattern of waveform and to depict signal phase and interferential beat frequencies.

12. The system of claim 1, wherein the vibration sources comprise at least one of electromagnetic drivers, transduc-ers, displacement shakers, linear resonance actuators, piezo-electric actuators, solenoids, pneumatic or hydraulic actua-tors, and electric motors with unbalanced weights, cams, or crankshafts.

13. The system of claim 1, wherein the mouthguard sensor is configured to provide a feedback signal to at least one of the first vibration source and the second vibration source in response to the super-imposed vibration.

14. The system of claim 1, further comprising a third vibration contact connected to a third vibration source and a fourth vibration contact connected to a fourth vibration source, wherein a location and orientation of the third vibration contact and a location and orientation of the fourth vibration contact are configured in a manner that vibrations from the third vibration source and the fourth vibration source combine to produce the super-imposed vibration.

15. The system of claim 1, wherein a controller is configured to execute a sequence of waveform parameters to produce a sequence of different perceived waveforms inside the subject over a period of time.

* * * * *